United States Patent
Min

(10) Patent No.: US 11,241,185 B2
(45) Date of Patent: Feb. 8, 2022

(54) RESONATING DEVICE AND METHOD OF INDIVIDUAL EEG COGNITIVE FREQUENCY, RECORDING MEDIUM FOR PERFORMING THE METHOD

(71) Applicant: Korea University Research and Business Foundation, Seoul (KR)

(72) Inventor: Byoung-Kyong Min, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 311 days.

(21) Appl. No.: 16/286,220

(22) Filed: Feb. 26, 2019

(65) Prior Publication Data
US 2019/0261877 A1    Aug. 29, 2019

(30) Foreign Application Priority Data

Feb. 26, 2018  (KR) .................. 10-2018-0023103
Jan. 22, 2019  (KR) .................. 10-2019-0008327

(51) Int. Cl.
*A61B 5/048* (2006.01)
*A61N 1/04* (2006.01)
(Continued)

(52) U.S. Cl.
CPC .......... *A61B 5/374* (2021.01); *A61B 5/291* (2021.01); *A61B 5/6803* (2013.01); *A61N 1/0456* (2013.01); *A61N 1/36025* (2013.01); *A61B 5/377* (2021.01); *A61B 5/6814* (2013.01); *A61M 2021/0072* (2013.01)

(58) Field of Classification Search
CPC ..... A61B 5/6814; A61B 5/291; A61B 5/6831; A61B 5/375; A61B 5/6803; A61B 5/377; A61B 5/374; A61N 1/0456; A61N 1/36025; A61M 2205/583; A61M 2230/10; A61M 2021/0055; A61M 2021/0072; A61M 2210/0693; A61M 21/00
See application file for complete search history.

(56) References Cited

U.S. PATENT DOCUMENTS

2009/0318826 A1* 12/2009 Green .................. A61B 5/0006
                                                                600/545
2019/0247662 A1*  8/2019 Poltroak ................ A61B 5/246

FOREIGN PATENT DOCUMENTS

JP       2003-135414 A    5/2003
KR    10-2002-0037579 A    5/2002
(Continued)

OTHER PUBLICATIONS

Korean Notice of Allowance dated Apr. 21, 2020, in connection with the Korean Patent Application No. 10-2019-0008327.
(Continued)

*Primary Examiner* — Christine H Matthews
*Assistant Examiner* — Joshua Daryl D Lannu
(74) *Attorney, Agent, or Firm* — Hauptman Ham, LLP

(57) ABSTRACT

Provided is a method for enhancing cognitive function based on individual cognitive frequency resonance that intentionally and selectively enhances a specific cognitive function by resonating with brain waves through brain stimulation using an electric current of the same frequency or waveform as individual cognitive frequency generated during a cognitive task, and the method includes executing, by a subject, a cognitive task.

12 Claims, 10 Drawing Sheets

(51) Int. Cl.
    *A61N 1/36*     (2006.01)
    *A61B 5/00*     (2006.01)
    *A61B 5/0478*     (2006.01)
    *A61B 5/374*     (2021.01)
    *A61B 5/291*     (2021.01)
    *A61M 21/00*     (2006.01)
    *A61B 5/377*     (2021.01)

(56) References Cited

FOREIGN PATENT DOCUMENTS

| | | |
|---|---|---|
| KR | 10-1249069 B1 | 3/2013 |
| KR | 10-2013-0101903 A | 9/2013 |
| KR | 10-2013-0142476 A | 12/2013 |
| KR | 10-1469878 B1 | 12/2014 |
| KR | 10-2015-0024753 A | 3/2015 |
| KR | 1020180021017 A | 2/2018 |
| KR | 101949079 B1 | 2/2019 |

OTHER PUBLICATIONS

Korean Notice of Allowance dated Jan. 22, 2019, in connection with the Korean Patent Application No. 10-2018-0023103.

* cited by examiner

RESONATING DEVICE AND METHOD OF INDIVIDUAL EEG COGNITIVE FREQUENCY, RECORDING MEDIUM FOR PERFORMING THE METHOD

CROSS-REFERENCE TO RELATED APPLICATIONS

This application claims priority under 35 U.S.C. § 119 to Korean Patent Application No. 10-2018-0023103, filed on Feb. 26, 2018, and Korean Patent Application No. 10-2019-0008327 filed on Jan. 22, 2019, in the Korean Intellectual Property Office, the disclosure of which is incorporated herein by reference in its entirety.

TECHNICAL FIELD

The present disclosure relates to a device and method for enhancing cognitive function based on individual cognitive frequency resonance and a recording medium for performing the method, and more particularly, to a device and method for enhancing cognitive function based on individual cognitive frequency resonance that generates individual unique frequency and brings it into resonance with brain waves and a recording medium for performing the method.

BACKGROUND

Electroencephalogram (EEG) refers to electrical activity generated in brain of animals including human, and various waveforms such as a-waves, slow waves or sleep spindle waves are found according to the state of brain activity.

Recently, studies are made to not only measure EEG but also induce brain waves by applying electrical stimulation non-invasively to the subject's head, and this electrical stimulation is referred to as Transcranial Current Stimulation (tCS).

The brain wave stimulation causes disturbance or resonance of specific brain wave to accelerate or suppress the brain activity for use in the field such as memory capacity improvement or mental disorder treatment.

However, the existing brain wave stimulation method as described above ambiguously identifies the full frequency band. For example, when stimulation frequency is theta wave frequency, the method evaluates the frequency band of 4-8 Hz as a whole, and thus it has an error that is inherent in averaging, and rather, undermines the individual unique frequency.

RELATED LITERATURES

Patent Literatures (Patent Literature 1) Korean Patent No. 10-1469878
(Patent Literature 2) Korean Patent No. 10-1249069

SUMMARY

An aspect of the present disclosure provides a device and method for enhancing cognitive function based on individual cognitive frequency resonance that measures individual cognitive frequency (ICF) in human generated when performing a specific cognitive function, generates the measured frequency using a transcranial current stimulator and brings it into resonance with brain waves to enhance brain function, and a recording medium for performing the method.

The technical problem of the present disclosure is not limited to the technical problem mentioned above, and another technical problem not mentioned herein will be clearly understood by those skilled in the art from the following description.

A method for enhancing cognitive function based on individual cognitive frequency resonance according to an embodiment of the present disclosure includes executing, by a subject, a cognitive task related to a specific cognitive function, measuring electroencephalogram (EEG) of the subject that is executing the cognitive task, analyzing power spectrum of the measured EEG of the subject for each frequency, setting a peak frequency having a highest amplitude value in each frequency band of the analyzed power spectrum as individual cognitive frequency (ICF) of the subject executing the cognitive task, and generating a same frequency or waveform as the peak frequency set as the individual cognitive frequency and bringing it into resonance with brain waves of the subject related to the specific cognitive function.

In an embodiment, the bringing into resonance may include generating an alternating current having the same frequency or waveform as the peak frequency set as the individual cognitive frequency.

In an embodiment, the bringing into resonance may include generating the same frequency or waveform as the peak frequency using a transcranial Current Stimulator (tCS).

In an embodiment, the bringing into resonance may include generating a pulse of the same frequency or waveform as the peak frequency using a Transcranial Magnetic Stimulator (TMS).

In an embodiment, the bringing into resonance may include generating ultrasound of the same frequency or waveform as the peak frequency using a low-intensity Focused Ultrasound Stimulator (FUS).

In an embodiment, the bringing into resonance may include generating a frequency to a brain part of the subject responsible for the specific cognitive function.

In an embodiment, the executing the cognitive task may include executing each of a first cognitive task related to a first cognitive function and a second cognitive task related to a second cognitive function that is different from the first cognitive function.

In an embodiment, the setting as the individual cognitive frequency may include setting individual cognitive frequency set through the execution of the first cognitive task as a first unique frequency, and individual cognitive frequency set through the execution of the second cognitive task as a second unique frequency.

In an embodiment, the bringing into resonance may include bringing a first unique frequency and a second unique frequency having different frequencies combined together into resonance with the brain waves of the subject at the same time.

In an embodiment, the executing the cognitive task may include executing the cognitive task of a plurality of cognitive functions in combination.

In an embodiment, the method for enhancing cognitive function based on individual cognitive frequency resonance may further include delivering non-invasive neurostimulation to the subject's brain through the frequency causing the resonance.

A computer-readable recording medium according to another embodiment of the present disclosure has recorded thereon a computer program for performing the method for enhancing cognitive function based on individual cognitive frequency resonance.

A device for enhancing cognitive function based on individual cognitive frequency resonance according to an embodiment of the present disclosure includes a cognitive task execution unit which allows a subject to execute a cognitive task related to a specific cognitive function, an EEG measuring unit which measures EEG of the subject that is executing the cognitive task, an EEG spectrum analysis unit which analyzes power spectrum of the measured EEG of the subject for each frequency, a frequency setting unit which sets a peak frequency having a highest amplitude value in each frequency band of the analyzed power spectrum as individual cognitive frequency (ICF) of the subject executing the cognitive task, and a frequency resonating unit which generates a same frequency or waveform as the peak frequency set as the individual cognitive frequency, and brings it into resonance with brain waves of the subject related to the specific cognitive function.

According to an aspect of the present disclosure described above, it is possible to immediately use in real life by virtue of a non-invasive method, and provide educational, social or economical effects, for example, increased learning and memory capacity through non-invasive brain stimulation.

DETAILED DESCRIPTION OF EMBODIMENTS

Figure 1:
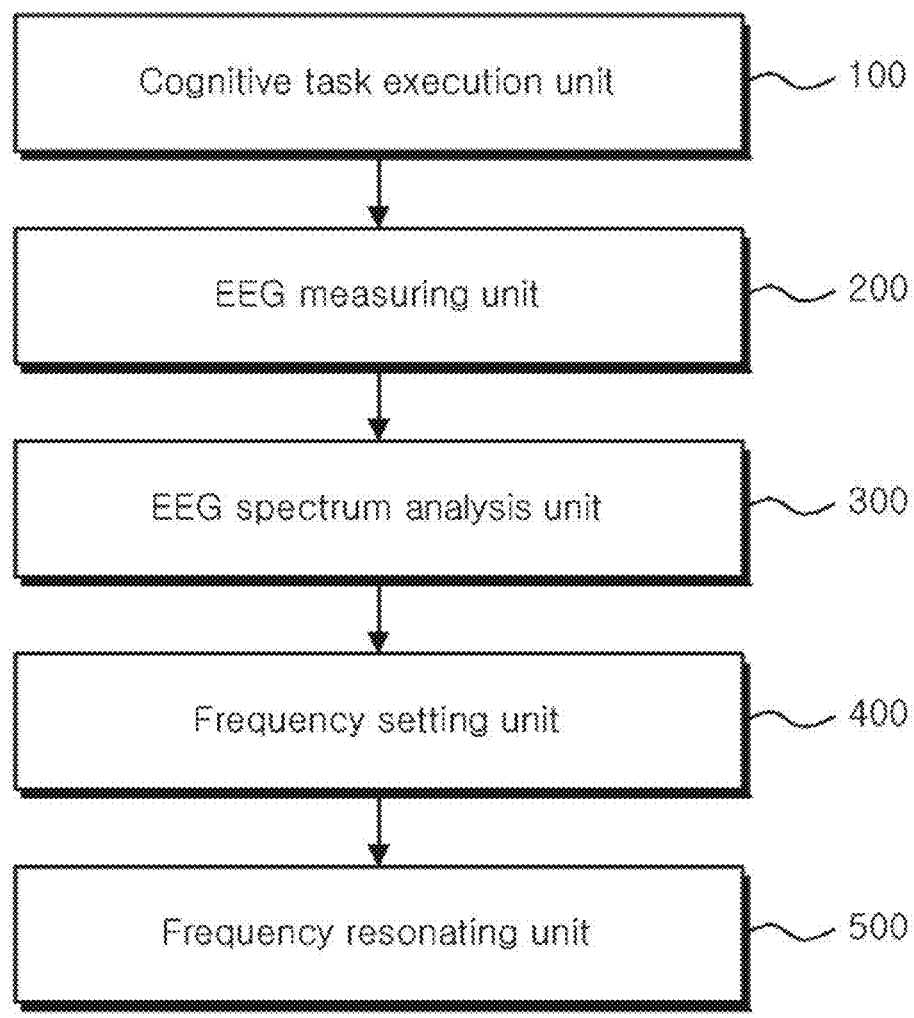
FIG. 1 is a schematic diagram showing configuration of a device for enhancing cognitive function based on individual cognitive frequency resonance according to an embodiment of the present disclosure.

The following detailed description of the present disclosure is made with reference to the accompanying drawings, in which particular embodiments for practicing the present disclosure are shown for illustration purposes. These embodiments are described in sufficiently detail for those skilled in the art to practice the present disclosure. It should be understood that various embodiments of the present disclosure are different but do not need to be mutually exclusive. For example, particular shapes, structures and features described herein in connection with one embodiment can be embodied in other embodiment without departing from the spirit and scope of the present disclosure. It should be further understood that changes can be made to locations or arrangements of individual elements in each disclosed embodiment without departing from the spirit and scope of the present disclosure. Accordingly, the following detailed description is not intended to be taken in limiting senses, and the scope of the present disclosure, if appropriately described, is only defined by the appended claims along with the full scope of equivalents to which such claims are entitled. In the drawings, similar reference signs denote same or similar functions in many aspects.

Hereinafter, exemplary embodiments of the present disclosure will be described in more detail with reference to the accompanying drawings.

FIG. 1 is a schematic diagram showing configuration of a device for enhancing cognitive function based on individual cognitive frequency resonance according to an embodiment of the present disclosure.

Referring to FIG. 1, the device for enhancing cognitive function based on individual cognitive frequency resonance includes a cognitive task execution unit 100, an electroencephalogram (EEG) measuring unit 200, an EEG spectrum analysis unit 300, a frequency setting unit 400 and a frequency resonating unit 500.

The cognitive task execution unit 100 allows a subject to execute a cognitive task related to a specific cognitive function.

Here, cognitive task execution may be performed by the subject spontaneously or in response to a request for the cognitive task through output means including audio means such as a speaker or display means such as a liquid crystal display (LCD) monitor.

The EEG measuring unit 200 measures EEG of the subject that is executing the cognitive task by the cognitive task execution unit 100.

In an embodiment, the EEG measuring unit 200 may be formed as an EEG measuring device that measures EEG through amplification, filtering and frequency analysis of electrical potential measured from electrodes contacting the scalp in a headset form or in a manner of attaching to the scalp. However, EEG measurement by the present disclosure is not limited to the above-described means, and the present disclosure is not limited to a particular type and includes any means for measuring human EEG.

The EEG spectrum analysis unit 300 analyzes the power spectrum of the EEG of the subject measured by the EEG measuring unit 200 for each frequency.

In an embodiment, the EEG spectrum analysis unit 300 is a device used in the EEG frequency analysis method, and may include a Fast Fourier Transform (FFT) spectrum analyzer or a wavelet analyzer (Wavelet Transformation) used in a wide range of applications.

The frequency setting unit 400 sets a peak frequency having a highest amplitude value in each frequency band of the power spectrum analyzed by the EEG spectrum analysis unit 300 as individual cognitive frequency (ICF) of the subject executing the corresponding cognitive task.

The frequency resonating unit 500 generates the same frequency or waveform as the peak frequency set as the individual cognitive frequency by the frequency setting unit 400, and brings it into resonance with brain waves of the subject related to the specific cognitive function.

In an embodiment, the frequency resonating unit 500 may generate the same frequency or waveform as the peak frequency using a transcranial Current Stimulator (tCS).

Figure 3:
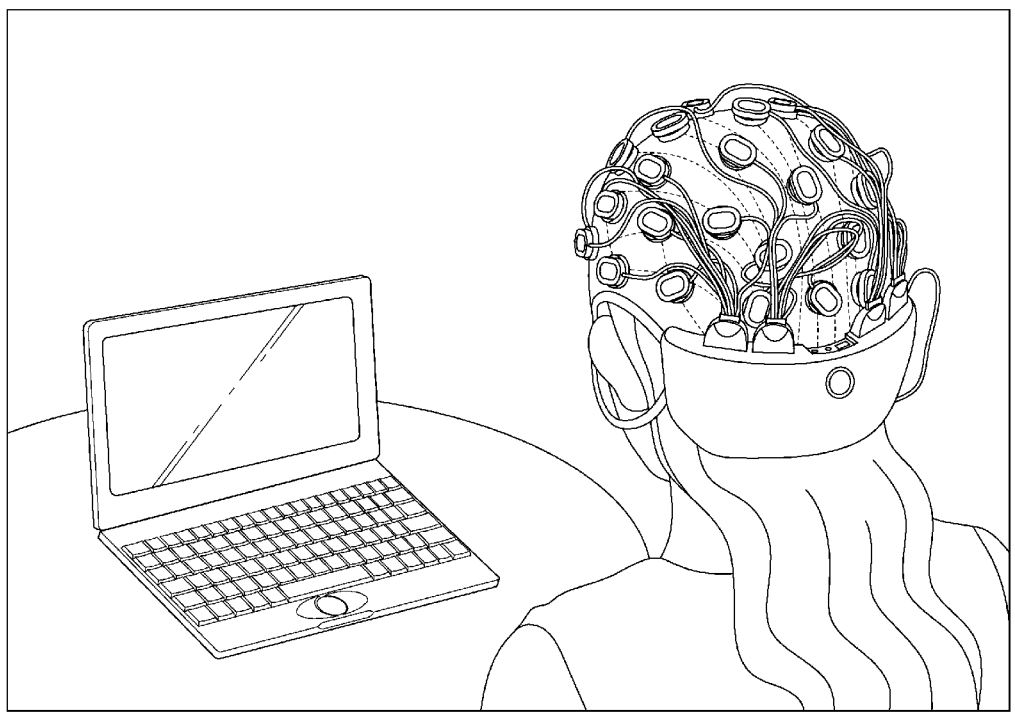
FIG. 3 is a diagram illustrating an example of a mounted transcranial current stimulator.
Figure 8:
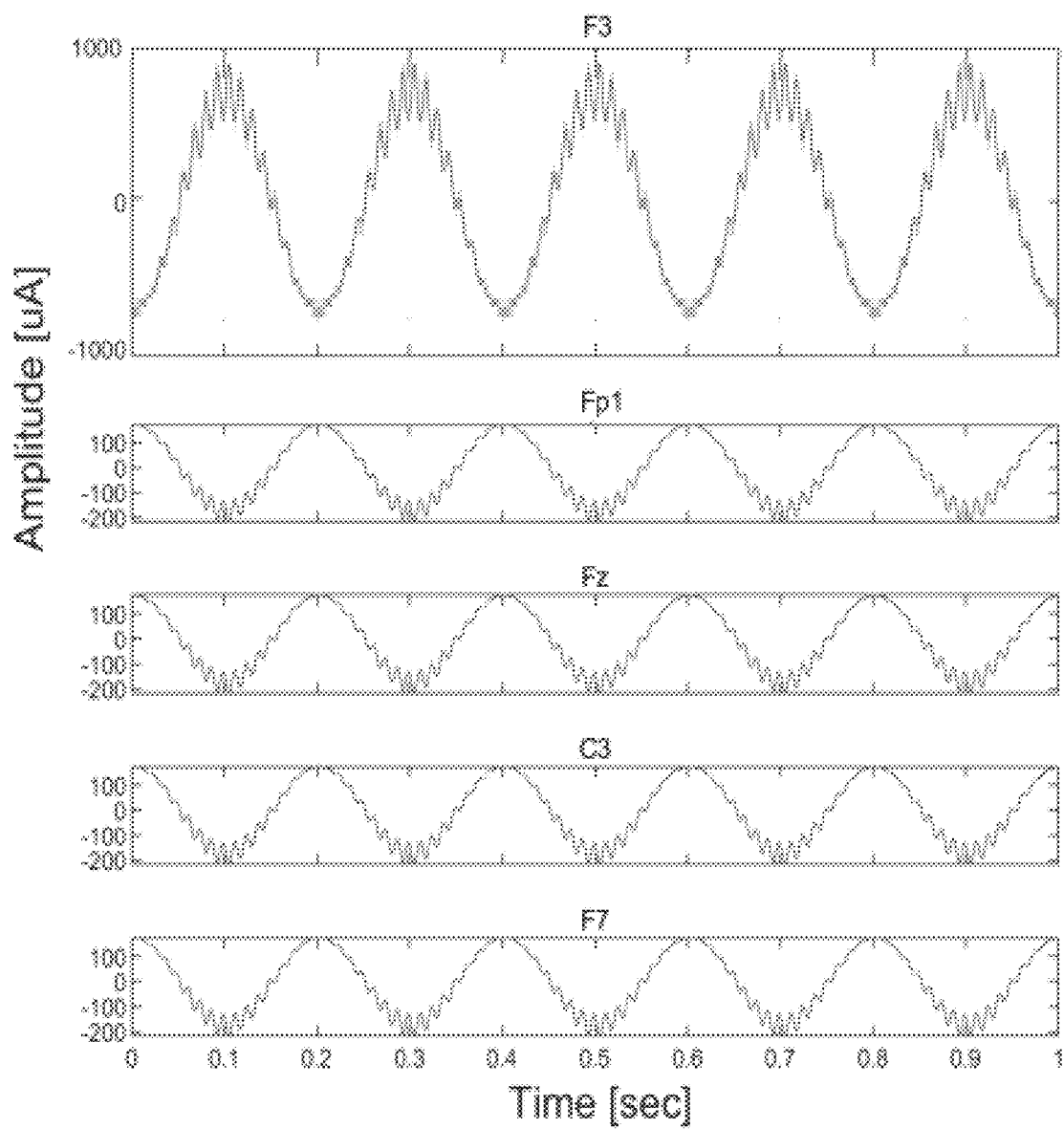
FIG. 8 is a waveform diagram of a theta-gamma Phase-Amplitude Coupling (PAC)-transcranial Alternating Current Stimulation (tACS) based electrical brain stimulation pattern model applied to the experiment.

Here, the transcranial current stimulator is a non-invasive neural function controller that intentionally controls a specific cognitive function by stimulating the brain with an electric current having a frequency band related to the corresponding cognitive function, and in particular, an alternating current (AC) can be used, and this is referred to as transcranial Alternating Current Stimulation (tACS) (see FIGS. 3 and 8).

The device for enhancing cognitive function based on individual cognitive frequency resonance having the above-described configuration may execute or create various software based on an Operation System (OS), namely, a system. The OS is a system program for enabling software to use the hardware of the device, and may include mobile computer OS including Android OS, iOS, Windows Mobile OS, Bada OS, Symbian OS and Blackberry OS and computer OS including Windows family, Linux family, Unix family, MAC, AIX and HP-UX.

The brain wave resonating method by each component of the device for enhancing cognitive function based on individual cognitive frequency resonance having the above-described configuration is described below in the description of the method of FIG. 2 and afterward.

Figure 2:
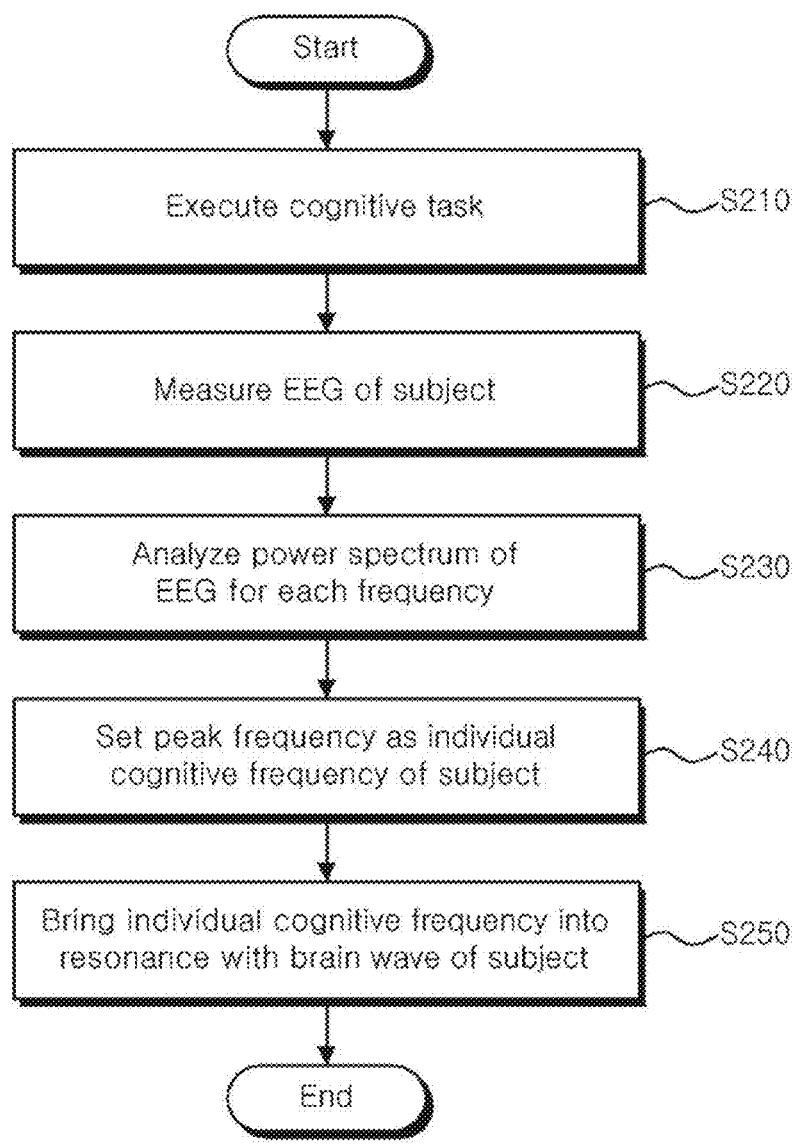
FIG. 2 is a flowchart illustrating a method for enhancing cognitive function based on individual cognitive frequency resonance according to an embodiment of the present disclosure.

FIG. 2 is a flowchart illustrating a method for enhancing cognitive function based on individual cognitive frequency resonance according to an embodiment of the present disclosure.

In general, brain wave components for each frequency are each related to their corresponding cognitive functions. For example, theta waves having frequency of 4-8 Hz are related to working memory, and alpha waves having frequency of 8-13 Hz are related to attention or inhibition function. In addition, delta waves of low frequency having DC-4 Hz are related to sleep function, and accordingly, attributes of human brain waves for each frequency selectively represent specific cognitive functions.

However, even the same frequency band has individual cognitive frequency (ICF) of the frequency reflecting the corresponding cognitive function individually to each subject.

Referring to FIG. 2, the resonating method of individual cognitive frequency begins with allowing the subject to execute a cognitive task related to a specific cognitive function (S210).

The cognitive task execution in the above-described S210 may be performed by the subject spontaneously or in response to a request for the cognitive task through output means including audio means such as a speaker or display means such as an LCD monitor.

The requested cognitive task in the above-described S210 may include a working memory task, an attention task or an inhibitory control task.

For example, in the case of working memory, the tester presents three or four unspecified numbers and requests the subject to memorize, and the subject needs to retain the corresponding information for a while. Subsequently, the tester presents a specific number to the subject and asks if this number is present in the previously presented numbers, and when the subject makes a correct response, may evaluate that the subject did the working memory correctly.

The EEG of the subject that is executing the cognitive task by the above-described S210 is measured (S220).

In an embodiment, the EEG measuring method in the above-described S220 may measure through an EEG measuring device that measures EEG through amplification, filtering and frequency analysis of electricity measured from electrodes contacting the scalp in a headset form or in a manner of attaching to the scalp. However, EEG measurement by the present disclosure is not limited to the above-described means, and the present disclosure is not limited to a particular type and includes any means for measuring human EEG.

The power spectrum (irregularly distributed spectrum density) for each frequency of the subject's EEG measured in the above-described S220 is analyzed (S230).

The EEG measured in the above-described S220 is analyzed for the power spectrum of the subject's EEG for each frequency to selectively extract a change of characteristic EEG related to the specific cognitive function by executing the cognitive task by the S210.

For analysis of the EEG measured in the above-described S220, a variety of brain signal analysis methods may be used.

First, Cross-Frequency Coupling (CFC) may analyze a relationship in which the phase of low frequency EEG controls the amplitude of high frequency EEG.

Second, Granger causality analysis of brain signals may analyze the effect of brain stimulation through Granger causality analysis between functionally interconnected brain areas.

Third, Time Frequency (TF) analysis may compare and analyze a time-frequency correlation of EEG signals for each experimental condition, and analyze the phase between the corresponding areas for each frequency component.

A peak frequency having a highest amplitude value in each frequency band of the power spectrum analyzed in the above-described S230 is set as individual cognitive frequency of the subject executing the cognitive task (S240).

That is, the present disclosure can provide brain wave resonance with higher reliability, taking individual variances in EEG attributes across subjects into account, by precisely identifying and using only individual cognitive frequency of the frequency individually reflecting the corresponding cognitive function even in the same frequency band, rather than selecting the corresponding full frequency band roughly.

Here, the individual cognitive frequency is an oscillation value of individual EEG frequency that individually and optimally reflects the cognitive function corresponding to the cognitive task executed in the above-described S210.

The existing techniques ambiguously identifies the full frequency band. For example, in the case of theta wave band, they evaluate 4-8 Hz as a whole unconditionally, and thus they have an error that is inherent in averaging, and may undermine the individual unique frequency.

To solve this problem, the present disclosure selectively identifies and uses a peak frequency that is an individual unique frequency different for each person, to provide an improved EEG measuring method and brain stimulation method over the existing methods, as well as a reasonable and scientific method in terms of EEG analysis.

A method of determining the individual cognitive frequency identifying the specific cognitive function set in the above-described S240 is as follows.

In general, through analysis of power spectrum for each frequency of EEG generated during a specific cognitive task, a peak frequency with a highest amplitude value in a frequency band best individually reflecting a cognitive function necessary for the corresponding cognitive task is determined to be individual cognitive frequency in the corresponding cognitive task.

For example, the working memory task is a task used to evaluate working memory in which the tester presents several unspecified numbers (or letters, symbols, spaces, etc.) and requests the subject to memorize, the subject needs to retain the corresponding information for a while, and then the tester presents a specific number (or letter, symbol, space, etc.) to the subject and asks if this number (or letter, symbol, space, etc.) is present in the previously presented numbers (or letters, symbols, spaces, etc.). In the case of this working memory task, if the subject has done correctly, the theta wave range of 4-8 Hz will be dominantly observed in EEG measured while the subject retains the corresponding information. This is because theta brain waves are closely related to working memory.

However, even though theta waves of 4-8 Hz are measured, in the case of EEG measured during the working memory task for each subject, there are individual variances across subjects, for example, the strong power spectrum in a person is seen at 5 Hz, and the strong power spectrum in another person is seen at 7 Hz.

Even though the subjects execute the same cognitive task, the individual cognitive frequency may differ in each subject during the corresponding cognitive task.

The individual cognitive frequency of the subjects having different individual cognitive frequencies may be easily measured by performing EEG power spectrum analysis such as Fast Fourier Transform (FFT) for each subject.

In the above-described S230, in an embodiment, association between the working memory function (one example of specific cognitive functions) of the subject and the measured individual cognitive frequency may be seen in real time using the working memory evaluation method such as the Sternberg task (a task for evaluating the subject's working memory capacity where the subject is asked to retain a specific list of items for a while, and then identify whether a specific item is present in the previous list) or the N-back task (a task for evaluating working memory where stimuli are consecutively presented, and the subject is asked whether stimulus appearing after $N^{th}$ stimulus of a specific stimulus is equal to stimulus appearing before $N^{th}$ stimulus in the presented list of stimuli).

For example, the 3-back task is a task in which the subject is presented number or letter stimuli one by one, and needs to decide if the current stimulus is the same as one presented third trials ago, and it also requires the subject to retain the corresponding information for a specific period of time, and can be used to evaluate working memory.

In addition, an attention related task or an inhibitory control task may be used.

The individual cognitive frequency by the present disclosure does not greatly change over time, and this is because anatomical structure of human brain and connection between brain areas are individually specific.

Accordingly, specific EEG frequency generated in the corresponding brain structure is unique and relatively stable over time.

However, the unique individual frequency in the corresponding frequency band even within a subject may change according to the type or level of a cognitive task, but the corresponding individual unique frequency will be stable in a constant cognitive task.

The same frequency or waveform as the peak frequency set as the individual cognitive frequency in the above-described S240 is generated and brought into resonance with the brain waves of the subject related to the specific cognitive function (S250).

In an embodiment, the step of bringing into resonance (S250) may generate an alternating current having the same frequency or waveform as the peak frequency set as the individual cognitive frequency.

The transcranial current stimulator as described below may use the alternating current frequency and the direct current frequency in an alternating manner. That is, an example is a method that increases the corresponding EEG potential to a specific level using the direct current, and makes changes using the alternating current. Also, in this case, however, because brain waves are generally oscillation waves (alternating current component), it is desirable to use the alternating current frequency.

In an embodiment, the step of bringing into resonance (S250) may generate the same frequency or waveform as the peak frequency using a transcranial Current Stimulator (tCS).

Here, the transcranial current stimulator is a non-invasive neural function controller designed to intentionally control a specific cognitive function by stimulating the brain with an electric current having a frequency band related to the corresponding cognitive function, and in particular, an alternating current (AC) can be used, and this is referred to as a transcranial Alternating Current Stimulator (tACS).

One of non-invasive neural function controllers that can be used in real life is a transcranial current stimulator as described above. The transcranial current stimulator can stimulate the brain in a non-invasive manner using not only the direct current (DC) but also the alternating current (AC), and oscillatory tDCS (otDCS) where the direct current (DC) is combined with the alternating current (AC) may be used. However, when considering that brain waves are oscillatory waves, it is desirable to stimulate the frequency band related to the specific cognitive function using the alternating current, thereby selectively and intentionally controlling the corresponding cognitive function.

Another brain stimulation method is Transcranial Magnetic Stimulation (TMS). The transcranial magnetic stimulator (TMS) may apply a single pulse at an accurate point in time, or may apply a magnetic field pulse by the patterned protocol in the same way as the repetitive transcranial magnetic stimulation (rTMS).

Still another brain stimulation method is low-intensity Focused Ultrasound Stimulation (FUS). The low-intensity Focused Ultrasound Stimulation (FUS) may apply stimulation with millimeter (mm)-scale spatial accuracy into the deeper regions of the brain due to a more accurate and precise focal point, compared to the existing Transcranial Magnetic Stimulation (TMS) and Transcranial Current Stimulation (tCS).

However, Transcranial Current Stimulation (tCS) is the most efficient method because it can resonate the brain waves most similarly to the brain wave shape.

The present disclosure generates the same alternating current frequency as the individual cognitive frequency identifying the corresponding cognitive function using the alternating current component of the non-invasive transcranial Alternating Current Stimulator (tACS), and brings it into resonance with the corresponding unique cognitive frequency in the brain, thereby selectively and intentionally controlling the enhancement or deterioration of the corresponding brain (cognitive or neural) function.

FIG. 3 is a diagram illustrating an example of a mounted transcranial current stimulator.

Referring to FIG. 3, it is possible to measure EEG while the subject wearing the transcranial current stimulator on the head is executing the corresponding cognitive task, and at the same time, it is possible to stimulate the brain by a non-invasive method by generating the same frequency or waveform as the peak frequency generated during the corresponding cognitive task.

Figure 4:
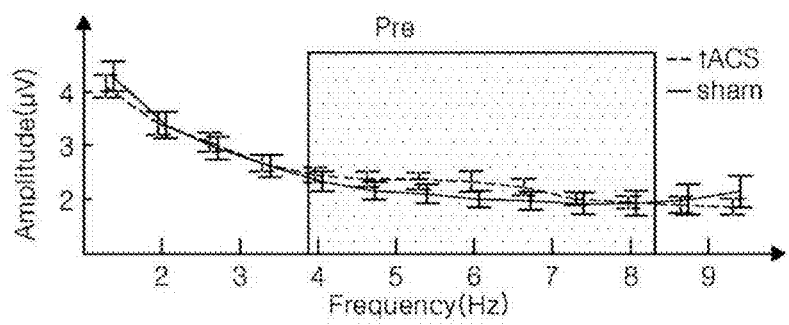
FIGS. 4 to 6 are graphs of changes in electroencephalogram (EEG) amplitude for each frequency, showing the effect of transcranial alternating current stimulation during Digit Span Task.
Figure 5:
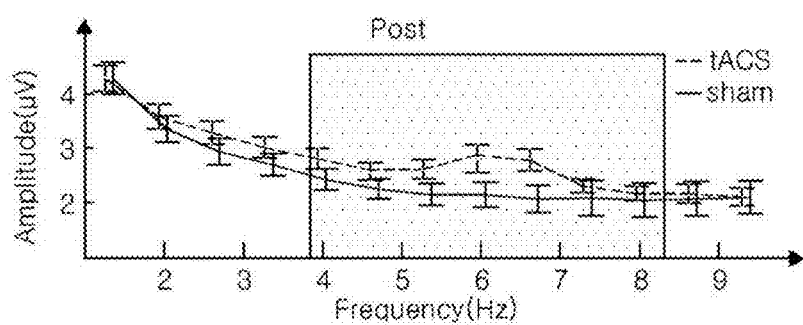
Figure 6:
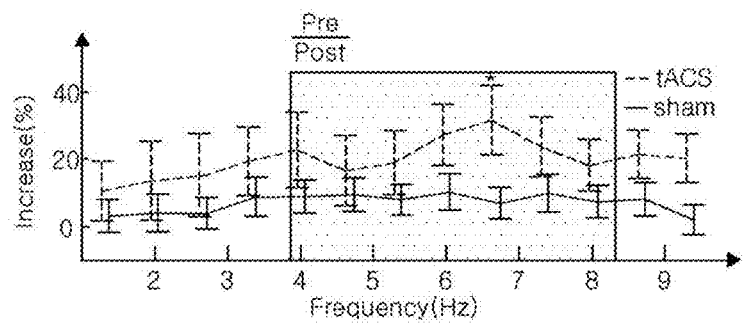

FIGS. 4 to 6 are graphs showing amplitude changes of Task-Related EEG by Digit Span Task before/after transcranial Alternating Current Stimulation measured by Christoph S. Herrmann et al. (2015, "Increase in short-term memory capacity induced by down-regulating individual theta frequency via transcranial alternating current stimulation").

In the graphs of FIGS. 4 to 6, the dotted line is an amplitude graph by tACS, and the solid line is an EEG amplitude graph for each frequency by the sham control protocol.

FIG. 4 is a graph showing the EEG amplitude by pre-stimulation, FIG. 5 is a graph showing the EEG amplitude by post-stimulation, and FIG. 6 is a graph showing a relative rate of increase in EEG amplitude from pre-stimulation to post-stimulation.

In FIGS. 4 to 6, the grey area denotes the statistically analyzed frequency region of interest between 4 Hz and 8 Hz, the error bar denotes ±1 standard deviation from the average, and the asterisk denotes a significant ($p<0.05$) difference between groups.

Referring to FIGS. 4 to 6, shown are a frequency-specific increase in amplitude in proportion to pre-stimulation (FIG. 4) and frequency spectrum from the digit span task of pre-stimulation (FIG. 4) and post-stimulation (FIG. 5), and a noticeable difference between two groups can be seen at 6.7 Hz.

In an embodiment, in the step of bringing into resonance (S250), resonance of the corresponding unique individual cognitive frequency may take place at the subject's brain region responsible for the specific cognitive function.

In general, brain regions consistently involved in general intelligence and its related working memory or cognitive capability such as reasoning are mainly disposed on the lateral side of the brain, whereas thinking about others and self mainly uses the medial side of the brain, and thus it is possible to achieve resonance with brain waves more efficiently by identifying the brain region responsible for the corresponding cognitive function and generating frequency.

Figure 7:
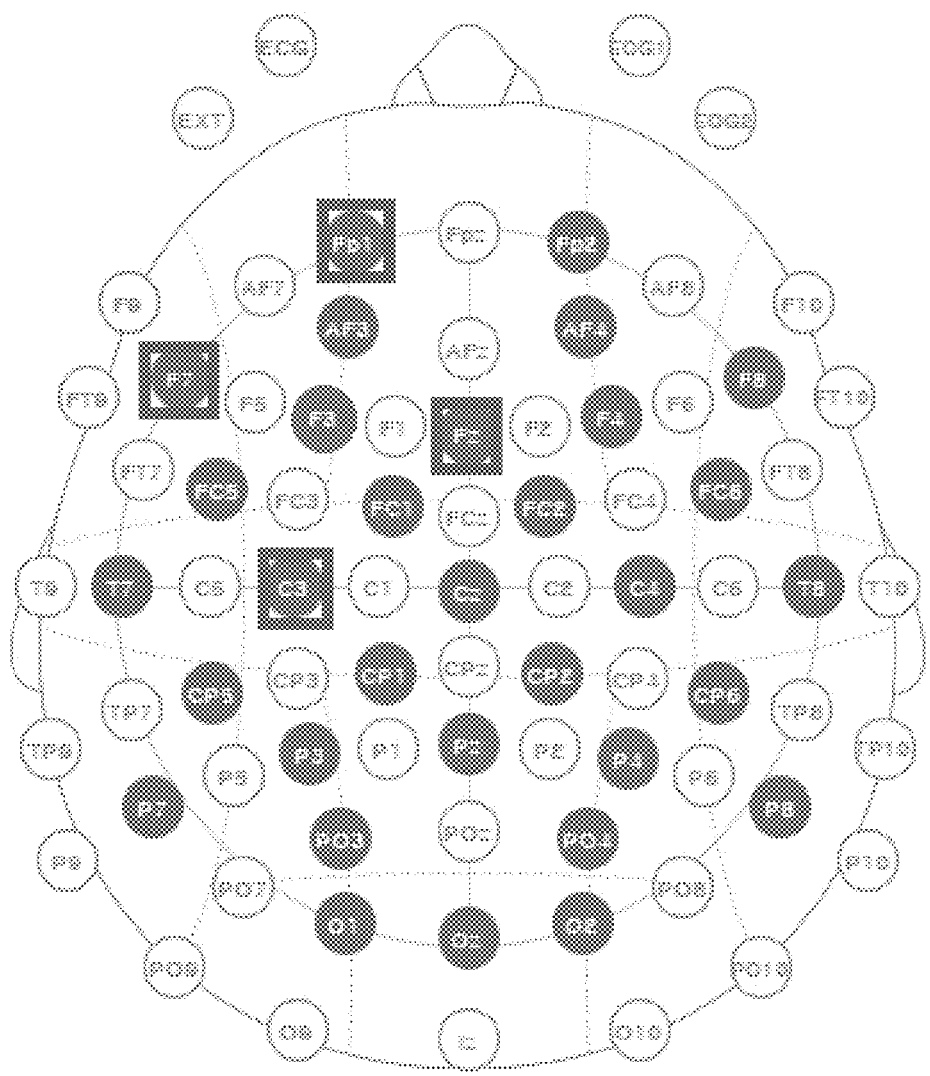
FIG. 7 is a diagram of an EEG cap model showing electrode positions of brain stimulation and EEG positions.

FIG. 7 is a diagram of an EEG cap model showing electrode positions of brain stimulation and EEG measurement positions.

Referring to FIG. 7, it can be seen that an EEG cap has 32 electrodes attached in contact with the scalp, and the electrodes are uniformly placed on the head by the 10-10 International standard system. The input impedance may be adjusted by injecting an electrode gel between the electrodes and the scalp. The EEG signals measured from the electrodes may be quantified at a predetermined interval through an amplifier.

In an embodiment, the main location of the brain mainly stimulated during the working memory task is the left prefrontal cortex. The electrode stimulated by the transcranial Alternating Current Stimulator (tACS) is the electrode F3 indicated by the thick circle at the upper left part of FIG. 7, and the electrode to which the stimulation current returns is electrodes Fp1, Fz, F7, C3 indicated by thick squares on the upper, lower, left and right sides around the stimulated electrode F3. However, this location is randomly set according to earlier research results, and is not limited to the corresponding location.

In an embodiment, in the step of executing the cognitive task (S210), a first cognitive task related to a first cognitive function, and a second cognitive task related to a second cognitive function that is different from the first cognitive function may be each executed.

However, the first cognitive task and the second cognitive task may be executed in any order, and if the first cognitive task and the second cognitive task are independently executed without each other's involvement, the tasks may be executed concurrently or asynchronously.

In an embodiment, in the step of setting as the individual cognitive frequency (S240), the individual cognitive frequency set through the execution of the first cognitive task may be set as a first unique frequency, and the individual cognitive frequency set through the execution of the second cognitive task may be set as a second unique frequency.

In an embodiment, in the step of brining into resonance (S250), the first unique frequency and the second unique frequency having different frequencies combined together may be brought into resonance (i.e., resonance using the frequency including the first unique frequency and the second unique frequency) with the brain waves of the subject at the same time.

The brain wave resonance by the present disclosure may be accomplished by individually bringing the first unique frequency and the second unique frequency having different frequencies (for example, resonate the first unique frequency, and then the second unique frequency, or vice versa) into resonance, and bringing the first unique frequency and the second unique frequency combined together into resonance with the brain waves of the subject at the same time as described above.

In an embodiment, in the step of executing the cognitive task (S210), a cognitive task of a plurality of cognitive functions in combination may be executed. For example, a cognitive task related to a complex C cognitive function in the combined form of A cognitive function and B cognitive function may be executed.

The method for enhancing cognitive function based on individual cognitive frequency resonance having the above-described steps may further include applying non-invasive neurostimulation to the subject's brain through the frequency that causes resonance.

The non-invasive neurostimulation according to the present disclosure may be performed through the transcranial current stimulator as described above. That is, the brain is stimulated with the electric current having the individual task-relevant frequency related to the specific cognitive function through the transcranial current stimulator, thereby intentionally controlling the enhancement or deterioration of the corresponding cognitive function, as well as improving the accuracy and reliability of the corresponding control.

The method for enhancing cognitive function based on individual cognitive frequency resonance having the above-described steps may improve the brain function such as executive function of the frontal lobe, decision making function, learning function, intelligence, creativity, quality of sleep and long-term memory.

FIG. 8 is a waveform diagram of a theta-gamma Phase-Amplitude Coupling (PAC)-tACS based electrical brain stimulation patter model applied to the experiment.

Referring to FIG. 8, X axis denotes the time in seconds (sec), Y axis denotes the amplitude (μA), and waveform denotes changes in amplitude of five electrodes F3, Fp1, Fz, F7, and C3 over time.

The transcranial Alternating Current Stimulator (tACS) may form a brain stimulation signal by applying an Individual Dominant Frequency (IDF) (for example, Individual Theta Frequency (ITF))-centered stimulation pattern based on Phase-Amplitude Coupling (PAC). The transcranial Alternating Current Stimulator (tACS) may present a current stimulation signal including a frequency change using the formed stimulation signal. The current stimulation signal is divided into stimulation onset period, stimulation continuation period and stimulation offset period.

Figure 9:
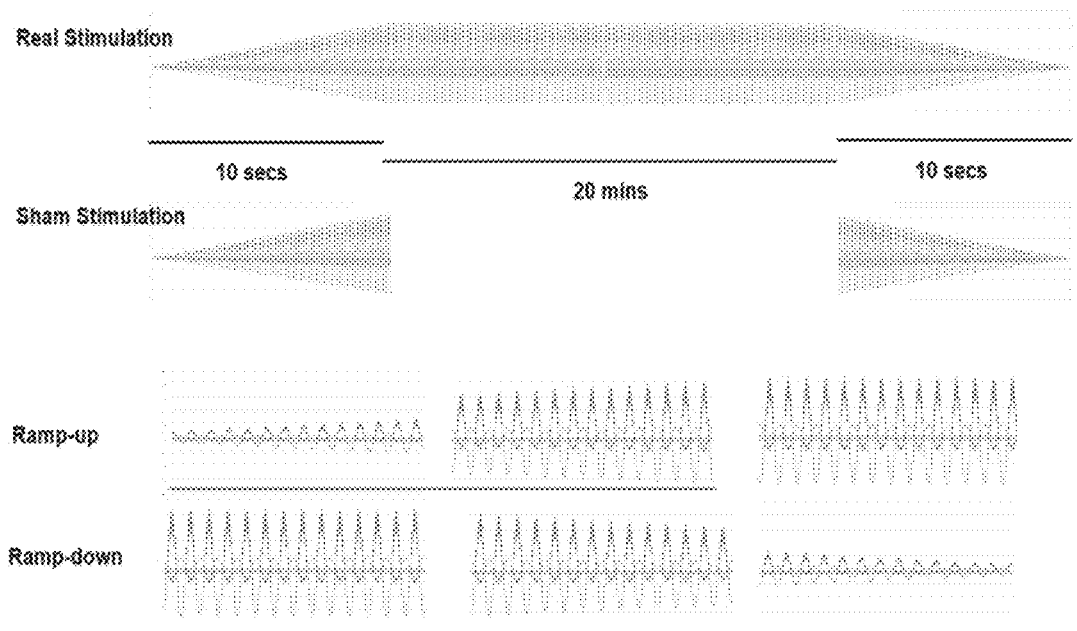
FIG. 9 is a schematic diagram of theta-gamma Cross-Frequency Coupling (CFC) tACS stimulation duration, and stimulation onset period (ramp-up), stimulation continuation period and stimulation offset period (ramp-down).

FIG. 9 is a schematic diagram of theta-gamma CFC tACS stimulation duration, and stimulation onset period (ramp-up), stimulation continuation period and stimulation offset period (ramp-down).

In an embodiment, the transcranial Alternating Current Stimulator (tACS) may stimulate the subject's brain for a total of 20 min 20 sec including each of the stimulation onset period (ramp-up) and the stimulation offset period (ramp-down) of 10 sec and the brain stimulation continuation period of 20 min.

In this instance, stimulation is applied to stim group (Real stimulation) for 20 min 20 sec, and stimulation is provided to sham group (Sham stimulation) only for the stimulation onset period (ramp-up) and the stimulation offset period (ramp-down). The subjects are divided into the control group (sham group) and the experimental group (stim group) to investigate if the brain function is improved by stimulation.

Figure 10:
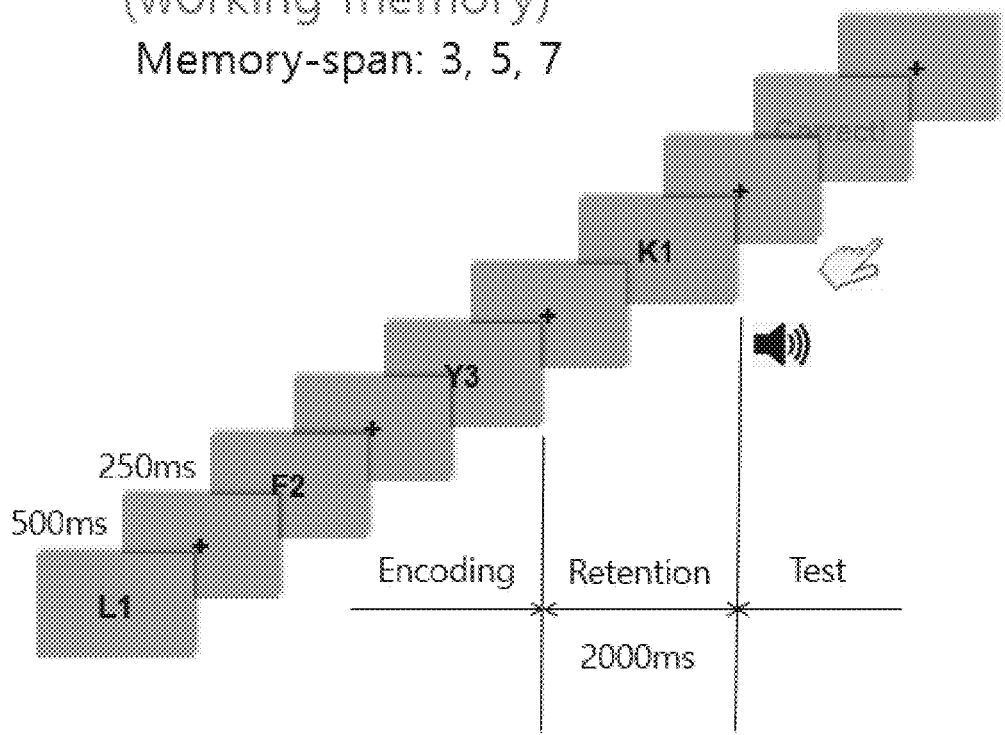
FIG. 10 is an exemplary diagram of a process of executing a working memory task under working load condition 3.

FIG. 10 is an exemplary diagram of a process of executing the Steinberg working memory task under working load condition 3.

The working memory load denotes the number of stimuli presented in the working memory task. That is, the larger number of stimuli the subject has to memorize for a while, the higher load applied to working memory of the subject. Working memory load 3 (W3) denotes three stimuli that the subject has to retain on the working memory, working memory load 5 (W5) denotes five, and working memory load 7 (W7) denotes seven. It is possible to gradually see the effect of brain stimulation on brain function improvement by changing the working memory load depending on the number of stimuli to memorize, presented in the working memory task.

The first step is the step of presenting a list of stimuli to memorize to request the subject to store (encode) the presented list of stimuli in working memory. In this instance, stimulation may be presented in a mixed form of English letter and number such as L1-F2-Y3.

The second step is the step of retaining memory. In an embodiment, the wait time is about 2 sec in the experiment, but the working memory retention time is not limited to 2 sec.

The third step is the step of determining whether the answer is correct or false. That is, after a predetermined working memory retention time passes, arbitrary test stimulation may be presented, and the working memory may be tested through the presence or absence of the stimulation in the previously presented list of stimuli.

The working memory enhancement provided by the brain stimulation method based on individual cognitive frequency resonance having the above-described steps may be considered in two aspects of reaction time and accuracy.

The reaction time (RT) denotes the time taken for the subject to select an answer after presenting test stimulation in the third step, and the unit is millisecond (ms).

Referring to Table 1, a change in reaction time before and after brain stimulation can be seen. The task execution speed (working memory processing speed) may be compared based on the reaction time. First, it can be seen that the reaction time (RT) is longer as the working memory load is higher. It can be seen that as the task is more difficult, it takes more time for the subject to respond. Second, it can be seen that the reaction time (RT) is quicker in the entire experimental group after brain stimulation. It is presumed that this feature results from the learning effect of repeated task execution. Third, it can be seen that reaction time (RT) reduction is greatest in STIM 7 group of the highest level of working memory. This feature shows that the brain stimulation method based on individual cognitive frequency resonance has the highest effect in the most difficult task.

TABLE 1

| Reaction time | Before brain stimulation | After brain stimulation |
| --- | --- | --- |
| STIM 3 | 732.46 ms | 661.09 ms |
| SHAM 3 | 682.42 ms | 589.48 ms |
| STIM 5 | 857.00 ms | 721.39 ms |
| SHAM 5 | 757.30 ms | 709.23 ms |
| STIM 7 | 886.84 ms | 747.01 ms |
| SHAM 7 | 791.34 ms | 780.07 ms |

Here, STIM denotes the group tested by actually stimulating the brain, and SHAM denotes the group to test without actually stimulating the brain. 3, 5, 7 following STIM and SHAM denote working memory load 3, working memory load 5 and working memory load 7, respectively.

Accuracy (%) denotes a ratio of correct responses to the total responses of the subject.

Referring to Table 2, a change in accuracy before and after brain stimulation can be seen. First, it can be seen that accuracy is lower as the working memory load is higher. It means that when the subject executes the task, as the task is more difficult, there is a higher possibility that the subject is wrong. Second, it can be seen that accuracy is higher in the entire experimental group after brain stimulation. It is presumed that this feature results from the learning effect of repeated task execution. Third, it can be seen that accuracy improvement in STIM 7 group is greatest. This feature shows that the brain stimulation method based on individual cognitive frequency resonance has the highest effect in the most difficult task.

TABLE 2

| Accuracy | Before brain stimulation | After brain stimulation |
| --- | --- | --- |
| STIM 3 | 94.98% | 96.89% |
| SHAM 3 | 92.13% | 93.80% |
| STIM 5 | 79.63% | 84.96% |
| SHAM 5 | 80.39% | 86.97% |
| STIM 7 | 74.06% | 83.89% |
| SHAM 7 | 71.75% | 77.11% |

Here, STIM denotes the group tested by actually stimulating the brain, and SHAM denotes the group to test without actually stimulating the brain. 3, 5, 7 following STIM and SHAM denote working memory load 3, working memory load 5 and working memory load 7, respectively.

The method for enhancing cognitive function based on individual cognitive frequency resonance having the above-described steps is a challenging field, and it is reported that sleep function is enhanced by inducing brain wave resonance in rats using optogenetics, or the influence of transcranial Current Stimulator on the corresponding brain waves is maintained for about 90 min. However, it is yet insufficient to selectively control the corresponding cognitive function in an intended direction with reliability by resonating human individual cognitive frequency using a transcranial Current Stimulator.

For example, sleep spindle waves appears during deep sleep and are deficient in insomnia, and it is possible to overcome insomnia by perform control to artificially generate more sleep spindle waves in humans by using the present disclosure based on transcranial Current Stimulation-EEG resonance.

Additionally, in a view of the recent report of animal experiments about memory capacity enhancement by coupling between sleep spindle waves in the thalamus and slow waves in the cerebral cortex, human memory capability can be enhanced by the non-invasive brain wave resonating method through the present disclosure.

The method of enhancing cognitive function based on individual cognitive frequency resonance as described above may be implemented in the form of applications or program commands that may be executed through various computer components and may be recorded in computer-readable recording media. The computer-readable recording media may include program commands, data files and data structures, alone or in combination.

The program commands recorded in the computer-readable recording media may be specially designed and configured for the present disclosure, and may be those known and available to those having ordinary skill in the field of computer software.

Examples of the computer-readable recording media include hardware devices specially designed to store and execute program commands, for example, magnetic media such as hard disk, floppy disk and magnetic tape, optical recording media such as CD-ROM and DVD, magneto-optical media such as floptical disk, and ROM, RAM and flash memory.

Examples of the program command include machine code generated by a compiler as well as high-level language code that can be executed by a computer using an interpreter. The hardware device may be configured to act as one or more software modules to perform the processing according to the present disclosure, or vice ver.

While the embodiments of the present disclosure have been hereinabove described with reference to the embodiments, it will be appreciated by those skilled in the art that various modifications and changes may be made to the present disclosure without departing from the spirit and scope of the present disclosure set forth in the appended claims.

According to the present disclosure, it can be immediately used in real life through non-invasive brain wave resonance, and educational, social or economical effects, for example, increased learning and memory capacity, are expected through non-invasive brain stimulation.

DETAILED DESCRIPTION OF MAIN ELEMENTS

100: Cognitive task execution unit
200: EEG measuring unit
300: EEG spectrum analysis unit
400: Frequency setting unit
500: Frequency resonating unit

What is claimed is:

1. A method for enhancing cognitive function based on individual cognitive frequency resonance, comprising:
    executing, by a subject, a cognitive task related to a specific cognitive function;
    measuring an electroencephalogram (EEG) of the subject that is executing the cognitive task;
    analyzing a power spectrum for each frequency band of the measured EEG of the subject;
    setting a peak frequency having a highest amplitude value in the analyzed power spectrum for each frequency band as an individual cognitive frequency (ICF) of the subject executing the cognitive task; and
    generating a same frequency or waveform as the peak frequency set as the individual cognitive frequency, and bringing the generated frequency or waveform into resonance with brain waves of the subject related to the specific cognitive function.

2. The method for enhancing cognitive function based on individual cognitive frequency resonance according to claim 1, wherein the bringing into resonance comprises generating an alternating current having the same frequency or waveform as the peak frequency set as the individual cognitive frequency.

3. The method for enhancing cognitive function based on individual cognitive frequency resonance according to claim 1, wherein the bringing into resonance comprises generating the same frequency or waveform as the peak frequency using a transcranial Current Stimulation (tCS).

4. The method for enhancing cognitive function based on individual cognitive frequency resonance according to claim 1, wherein the bringing into resonance comprises generating a pulse of the same frequency or waveform as the peak frequency using a Transcranial Magnetic Stimulation (TMS).

5. The method for enhancing cognitive function based on individual cognitive frequency resonance according to claim 1, wherein the bringing into resonance comprises generating ultrasound of the same frequency or waveform as the peak frequency using a low-intensity Focused Ultrasound Stimulation (FUS).

6. The method for enhancing cognitive function based on individual cognitive frequency resonance according to claim 1, wherein the bringing into resonance comprises generating a frequency to a brain region of the subject responsible for the specific cognitive function.

7. The method for enhancing cognitive function based on individual cognitive frequency resonance according to claim 1, wherein the executing the cognitive task comprises executing each of a first cognitive task related to a first cognitive function and a second cognitive task related to a second cognitive function that is different from the first cognitive function.

8. The method for enhancing cognitive function based on individual cognitive frequency resonance according to claim 7, wherein the setting as the individual cognitive frequency comprises setting the individual cognitive frequency set through the execution of the first cognitive task as a first unique frequency, and the individual cognitive frequency set through the execution of the second cognitive task as a second unique frequency.

9. The method for enhancing cognitive function based on individual cognitive frequency resonance according to claim 7, wherein the bringing into resonance comprises bringing a first unique frequency and a second unique frequency having different frequencies combined together into resonance with the brain waves of the subject simultaneously.

10. The method for enhancing cognitive function based on individual cognitive frequency resonance according to claim 1, wherein the executing the cognitive task comprises executing the cognitive task of a plurality of cognitive functions in combination.

11. The method for enhancing cognitive function based on individual cognitive frequency resonance according to claim 1, further comprising:
- delivering non-invasive neurostimulation to the subject's brain through the generated frequency or waveform causing the resonance.

12. A device for enhancing cognitive function based on individual cognitive frequency resonance, comprising:
- a cognitive task execution unit which allows a subject to execute a cognitive task related to a specific cognitive function;
- an electroencephalogram (EEG) measuring unit which measures an EEG of the subject that is executing the cognitive task;
- an EEG spectrum analysis unit which analyzes a power spectrum for each frequency band of the measured EEG of the subject;
- a frequency setting unit which sets a peak frequency having a highest amplitude value in the analyzed power spectrum for each frequency band as an Individual Cognitive Frequency (ICF) of the subject executing the cognitive task; and
- a frequency resonating unit which generates a same frequency or waveform as the peak frequency set as the individual cognitive frequency, and brings the generated frequency or waveform into resonance with brain waves of the subject related to the specific cognitive function.

* * * * *